United States Patent
Munro, III et al.

(10) Patent No.: US 6,400,796 B1
(45) Date of Patent: Jun. 4, 2002

(54) X-RAY EMITTING SOURCES AND USES THEREOF

(75) Inventors: John J. Munro, III, North Andover; David C. Medich, Lowell, both of MA (US)

(73) Assignee: Implant Sciences Corporation, Wakefield, MA (US)

( * ) Notice: Subject to any disclaimer, the term of this patent is extended or adjusted under 35 U.S.C. 154(b) by 0 days.

(21) Appl. No.: 09/772,749

(22) Filed: Jan. 30, 2001

(51) Int. Cl.[7] ............................................. H01J 35/14
(52) U.S. Cl. ............................................. 378/64; 600/7
(58) Field of Search ................... 378/64, 65, 119, 378/143; 600/3, 7

(56) References Cited

U.S. PATENT DOCUMENTS

| | | | |
|---|---|---|---|
| 3,351,049 A | 11/1967 | Lawrence | 128/1.2 |
| 4,827,498 A * | 5/1989 | Parsons et al. | 378/119 |
| 5,369,679 A * | 11/1994 | Sliski | 378/65 |
| 5,729,583 A * | 3/1998 | Tang et al. | 378/122 |
| 5,840,064 A | 11/1998 | Liprie | 604/96 |
| 6,024,690 A | 2/2000 | Lee et al. | 600/3 |
| 6,071,227 A | 6/2000 | Popowski et al. | 600/3 |
| 6,234,257 B1 * | 11/2001 | Halavee | 378/121 |

* cited by examiner

Primary Examiner—Robert H. Kim
Assistant Examiner—Irakil Kiknadze
(74) Attorney, Agent, or Firm—Foley, Hoag & Eliot, LLP

(57) ABSTRACT

A device for treating an occlusion or constriction, such as a stenosis in a blood vessel or other conduit within the body, as well as for treating a tumor or cancerous area occurring around a conduit or duct in the body is provided. The device includes an insert having a non-radioactive precursor, and a capsule encapsulating the insert. The precursor, containing tungsten which is substantially enriched in tungsten-180, can be activated to emit X-ray radiation and delivered to the treatment site to treat the stenosis or cancerous area. Upon activation by exposure to neutron flux, tungsten-180 is transmuted to contain an amount of X-ray-emitting tungsten-181 sufficient for treatment. The tungsten can also act as an X-ray-opaque marker to facilitate external visualization of capsule after delivery to the treatment site.

33 Claims, 1 Drawing Sheet

X-RAY EMITTING SOURCES AND USES THEREOF

FIELD OF THE INVENTION

The present invention relates to therapeutic radioactive devices and methods of use thereof, and more particularly, to devices and methods for providing a radiation source for temporary application in the treatment of stenosis and/or brachytherapy.

BACKGROUND ART

Various techniques have been developed to treat many different conduits in the body when these conduits have become reduced in size due to the existence of a stenosis or when these conduits have been completely occluded.

With respect to vascular conduits, angioplasty has been used to open an artery or blood vessel in the region where the stenosis or the occlusion has occurred. A typical angioplasty procedure includes making a small incision through the body and into, for example, a blood vessel, and then maneuvering a guide wire through the vascular system to a point beyond the stenosis or occlusion within the blood vessel. A catheter with a balloon near its distal end can subsequently be threaded over the guide wire and advanced to the point of stenosis or occlusion. The balloon may thereafter be inflated and deflated several times, if necessary, to widen the constricted area within the blood vessel, and may thereafter be withdrawn from the body. In certain cases, a stent may be deployed to the now widened area within the blood vessel to mechanically maintain a channel across the previously constricted area.

However, despite the initial observed reduction in the area of stenosis or occlusion as a result of angioplasty, many patients unfortunately exhibit a reoccurrence of the stenosis within a few months of the original procedure.

Although the original stenosis is thought to occur by means of the build up of plaque over a relatively long period of time, it is now believed that the recurrence of the stenosis after the original angioplasty procedure may be unrelated to the cause of the original stenosis. It is believed that the inflation of the balloon catheter used in the angioplasty procedure or the placement of a stent in the area of the stenosis may cause irritation to the blood vessel, which can subsequently cause hyperplasia (i.e., inducing the blood vessel cells to rapidly reproduce), resulting in restenosis.

It has been proposed that if the site of stenosis in the blood vessel were treated with a radiation dose, the mechanism that causes hyperplasia may be destroyed without harming the blood vessel itself. During this procedure, it should be noted that it is important to precisely control the amount of radiation that is directed to the blood vessel wall, since too little radiation could actually induce hyperplasia within the irritated vessel, while too much radiation could destroy a portion of the blood vessel.

U.S. Pat. No. 5,840,064 issued to Liprie, discloses a method and apparatus for introducing radiation to the site of a stenosis in a blood vessel to endeavor to prevent restenosis and claims a device for treating an occlusion or a constriction in a vessel or other conduit in the body wherein said radioactive source is cesium-137, cobalt-60, iodine-125, iodine-131, cobalt-57, iridium-192, gold-198, palladium-103, strontium-89, strontium-90, phosphorus-32, or yttrium-90.

U.S. Pat. No. 6,024,690 issued to Lee et al. discloses a radiation source with delivery wire for delivering a dose of radiation to a treatment site within a vessel. The radiation source comprises a radioactive segment that includes rhenium having a half-life of less than approximately one hundred (100) hours.

U.S. Pat. No. 6,071,227 issued to Popowski et al. discloses medical appliances for the treatment of blood vessels by means of ionizing radiation and claims a medical appliance wherein the radioactive radiation emitter is the beta radiation emitter Yttrium-90.

Various therapeutic techniques have also been developed for treatment of tumorous, pre-cancerous, or other diseased tissue. One technique, known as brachytherapy, places radioactive sources at or near the treatment site to provide site-specific delivery of radiation therapy, potentially reducing undesirable side effects associated with teletherapy, such as irradiation of healthy tissue. A common brachytherapy technique uses catheters to deliver radiation to the treatment site. In this technique, numerous catheters may be simultaneously inserted into the treatment site, sewn into place, loaded with solid isotopic pellets for a prescribed time, and then removed. The process of placing a number of catheters simultaneously within the appropriate region is cumbersome and time-intensive. Additionally, invasive insertion and external exposure of the catheters presents an increased risk of infection to the patient, and can result in significant discomfort for the patient during treatment. Finally, any subsequent treatment, for example, treatment following tumor recurrence, requires that the entire process be repeated from the beginning.

Another common brachytherapy technique employs radioactive implants to deliver radiation therapy. In this technique, numerous radioactive pellets or seeds are implanted directly into the treatment site. However, the radiation fields generated by the implants are typically highly non-uniform, resulting in highly non-uniform distributions of radiation dose across the treatment site.

Although somewhat useful, the radionuclides provided above, along with those generally used in brachytherapy and/or the treatment of stenosis, can have certain undesirable effects. For example, beta-emitting radionuclides, such as strontium-89, strontium-90, phosphorus-32, yttrium-90 and rhenium-188 suffer from rapid dose drop-off within the blood vessel to be treated. Moreover, the dose perturbation due to the presence of a calcified plaque or a metallic stent is significant for the beta source. The dose reduction in the region beyond a plaque or a stent could be more than 20%. This reduction can result in significant underdosing and affect the outcome of the treatment Low energy gamma-emitting radionuclides, on the other hand, such as iodine-125 and palladium-103, experience even more significant dose perturbation due to the presence of a calcified plaque or a metallic stent.

High energy gamma-emitting radionuclides, such as cesium-137, cobalt-60, iodine-131, cobalt-57, iridium-192 and gold-198 are characterized by a significant potential for excessive whole-body dose to the patient, the cardiologist and the staff. Radiation safety considerations require the use of heavy lead shields to reduce exposure rates within the catheterization laboratories. Adequate shielding of catheterization laboratories to provide radiation protection to clinicians, as well as personnel outside the laboratory is a significant and costly task.

Accordingly, it is desirable to provide a radiation source which can be implanted at a treatment site to provide a sufficient uniform dose distribution throughout the surrounding tissue, even in the presence of calcification and/or of a stent, with a sufficiently long half-life to adequately treat the patients.

SUMMARY OF THE INVENTION

In accordance with an embodiment of the present invention, a source for delivering radiation, for instance, X-ray radiation, to a treatment site is provided. The source includes at least one insert having tungsten enriched with tungsten-180 and a capsule within which the insert is placed. The tungsten, in one embodiment, may be enriched to include at least about 30 atomic percent of tungsten-180 and is capable of being activated, so as to transform a portion thereof to an amount of X-ray emitting tungsten-181 with a radiation dose rate sufficient for treatment within a period of one hour. The insert, in certain embodiments, may be provided with a central core around which the tungsten-180 may be placed. The X-ray radiation emitted preferably has a range of from about 50 keV to about 70 keV. The capsule, similarly, may be made from a material that permits X-ray radiation in the range of from about 50 keV to about 70 keV to pass therethrough. In addition, as the capsule may be irradiated to activate the insert therein, the capsule should include materials that contain minimally acceptable amounts of isotopes that can be transmuted into radioactive isotopes that emit undesirable radiations. Moreover, if transmutation does occur, the radioactive isotopes should have such short half-lives or very low dose rates that their activities have little effect on healthy tissue.

In accordance with another embodiment, the present invention provides a method for generating radiation for treatment of diseased tissues. The method includes providing at least one insert having tungsten enriched with tungsten-180 that is capable of being activated to transform a portion thereof to an amount of X-ray-emitting tungsten-181. Next, the insert may be encased within a capsule. Once encased, the capsule and the insert therein may be exposed to a neutron flux, so as to transform a portion of the tungsten-180 to an amount of X-ray-emitting tungsten-181 with a radiation dose rate sufficient for treatment within a period of one hour. In an alternate embodiment, the insert may be irradiated prior to encasing the insert within the capsule. The irradiated insert, along with the capsule, may thereafter be delivered to the diseased tissue site for treatment, and removed once treatment is completed.

DETAILED DESCRIPTION OF SPECIFIC EMBODIMENTS

Figure 1:
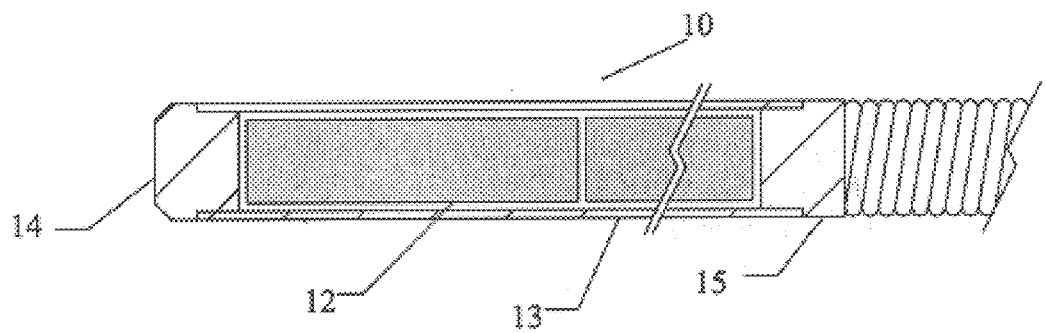
FIG. 1 illustrates a longitudinal section view a capsule having an X-ray source in accordance with one embodiment of the present invention.

The present invention provides, in accordance with one embodiment, a device for delivering radiation to a treatment site. Such a device may be provided, as illustrated in FIG. 1, as capsule 10 for temporary delivery to a selected treatment site to emit localized radiation, for example, X-ray or gamma ray radiation, for brachytherapy and/or the treatment of stenosis. The capsule 10, in one embodiment, comprises at least one insert 12 that includes a non-radioactive precursor material, distributed substantially throughout the insert 12, that is capable of being activated to produce X-ray-emitting tungsten-181.

Tungsten-181, in general, has a low energy radiation spectrum, primarily low-energy X-ray emissions in the 55–65 keV range, and a relatively long half-life of approximately 121 days. Because of these characteristics, tungsten-181 can be a good temporary radiation source for use in brachytherapy and/or the treatment of stenosis. In comparison, iridium-192, the currently preferred radioactive isotope for cardiovascular radiation treatment by temporary application, has a much higher radiation spectrum and a relatively short half-life of approximately 74 days. Thus, the softer and relatively low energy radiation spectrum of tungsten-181 allows for better radial dose distribution of the radiation to the treatment site, while the relatively longer half-life of tungsten-181 increases the useful lifetime of the radiation source to provide important advantages with respect to the economics of patient care. It should be appreciated that radiation energy in the range of from about 20 keV to about 100 keV, and more specifically, in the range of from about 50 keV to about 70 keV works well with present invention.

Tungsten-181, however, has not traditionally been used as a radiation source because of the practical difficulties involved in providing tungsten in an active form with suitable source strength to permit temporary application to the patient. In particular, since naturally occurring tungsten contains approximately 0.13 atomic percent of tungsten-180, if the naturally occurring tungsten were to be irradiated by neutron flux, so as to convert (i.e., transmute) the small amount of the tungsten-180 to tungsten-181, the amount of naturally occurring tungsten required to produce an X-ray intensity sufficient for treatment of a patient would be of a size far in excess of what could be delivered to the treatment site within a blood vessel. In addition, the issue of isotope enrichment must be considered. Specifically, naturally occurring tungsten contains other isotopes, such as, tungsten-184 and tungsten-186, that when irradiated by neutron flux, would be transmuted to other radioactive isotopes of tungsten, for instance, tungsten-185, tungsten-187, and tungsten-188. Such isotopes are known to have undesirable radioactive properties and are known to emit undesirable radiations for the treatment of blood vessels.

Another important consideration in the production of a radiation source in which tungsten-181 is the X-ray-emitting isotope is the self-shielding effect of tungsten. Although tungsten-181 emits X-rays, its isotopes are known to absorb substantial amounts of X-rays. Accordingly, the amount of tungsten-181 must be sufficiently large to compensate for this self-shielding effect, and to provide a dose rate suitable for the temporary treatment of a blood vessel.

Referring again to FIG. 1, in one embodiment, a plurality of inserts 12 may be positioned within the capsule 10. Each of inserts 12 may be provided with a shape that approximates the cylindrical interior of the capsule 10. By providing the insert with a cylindrical shape and by dispersing the non-radioactive precursor material which can be activated to produce X-ray-emitting tungsten-181 throughout the insert 12, a substantially uniform distribution of the X-ray radiation radially may be established. Although shown to be cylindrical, it should be noted that the inserts 12 can be provided with other shapes, including but not limited to wires or spheres, so long as the inserts 12 are capable of being placed within the capsule 10 and activated to produce X-ray-emitting tungsten-181. The inserts 12, while positioned within the capsule 10, may be sealed (i.e., encapsulated) within a tube 13 by a pair of end members or caps 14 and 15. The caps 14 and 15 may be securely attached to each end of tube 13 by methods known in the art, including welding. In this manner, direct contact with the radioactive materials in inserts 12 by human tissue may be prevented. Alternatively, inserts 12 may be encapsulated by plating or coating the inserts 12 with a non-radioactive material in a manner that would prevent direct contact with human tissue. Should it be desired, a combination of any of these components may be employed to encapsulate inserts 12. The components used in the encapsulation, in accordance with an embodiment of the invention, may be made from materials relatively non-absorbing of low energy X-ray radiation, so as not to interfere with the emission of the low-energy X-ray radiation from the inserts 12. In particular, the materials should permit X-ray radiation in the range of from about 50 keV to about 70 keV to pass therethrough. Such materials can included, for instance, highly purified aluminum, copper, vanadium, nickel and iron. Furthermore, the encapsulation components may be made from a biocompatible material that do not induce a toxic or allergic reaction when contacted with living tissue, or may be coated with a biocompatible coating. Suitable biocompatible materials include silicone polymers, organic polymers, titanium, carbon, stainless steel, tantalum, hafnium, zirconium, nickel-titanium alloy and combinations thereof. In this manner, in the unlikely event of a breach of the delivery catheter, the material will not affect the surrounding tissues prior to placement of the capsule 10 at the treatment site.

The non-radioactive precursor material distributed throughout inserts 12 that is capable of being activated to produce X-ray-emitting tungsten-181 includes, in one embodiment, tungsten which is substantially enriched in tungsten-180. For the purpose of the present invention, the tungsten used may be enriched with tungsten-180 to at least about 30 atomic percent, and can be enriched to as much as 99 atomic percent or upward. The enrichment of tungsten with tungsten-180 can be accomplished, in accordance with an embodiment of the invention, by electromagnetic separation, or by gas centrifuge separation or other isotope separation technique. Alternatively, tungsten that is enriched with tungsten-180 may be obtained, for example, from Oak Ridge National Laboratories.

It should be appreciated that enriched tungsten-180 does not necessarily have to be in elemental form. In fact, it may be provided compounded, mixed or alloyed with other materials. Indeed, during manufacturing of the insert 12, some of the tungsten can oxidize and form the compound tungsten oxide. The materials to be mixed, alloyed or compounded, therefore, should be chosen from those that contain minimally acceptable amounts of isotopes which, when irradiated by neutron flux, would be transmuted to radioactive isotopes that emit undesirable radiations for the treatment of blood vessels.

If these materials are nevertheless transmuted into radioactive isotopes that emit undesirable radiations, the isotopes should have such short half-lives or very low dose rates that their activities will have little or no consequence on healthy tissue. Materials which contain minimally acceptable amounts of undesirable radioactive isotopes or transmutable radioactive isotopes with short half-lives or very low dose rates include purified aluminum, copper, vanadium, nickel, iron, and/or oxygen. Furthermore, if a tungsten mixture, compound or alloy is used as the X-ray-emitting source, the mixture, compound or alloy should be substantially insoluble in aqueous solutions to prevent transfer of radioactive tungsten throughout the body in the unlikely event of a breach of the encapsulation and/or breach of a delivery catheter.

By providing the tungsten as a tungsten mixture, compound or alloy its fabrication and uniform distribution throughout the insert 12 may be facilitated. Specifically, when manufacturing the insert 12, the enriched tungsten, either alone or with other materials, may generally be provided in powder form with average particle sizes of between about 20 microns and about 200 microns. In one embodiment, metallic tungsten-180-enriched tungsten may be suitably mixed with powders of the other materials, and the resulting mixture may be pressed into insert 12, shown in FIG. 1 as being cylindrical in shape, at pressures sufficient to achieve at least about 75% of theoretical density. If desired, the pressed insert 12 may subsequently be heated to high temperatures, in a process known as sintering, so as to bind the particles of powder together to increase the density to about 95% of theoretical density. Alternatively, the enriched tungsten, either alone or with other materials, may be drawn into a solid wire or plated onto a wire, rather than pressed into an insert cylindrical in shape.

The amount of enriched tungsten to be provided in insert 12 can vary and depends upon the radiation dosage required for each treatment. For suitability for delivery through a blood vessel, the insert 12 and thus the capsule 10 should be as small as possible, while capable of producing a sufficient dose rate to provide the desired treatment dose within a period of less than one hour.

In order to insure that the X-ray-emitting insert 12 is delivered to the treatment site, so as to adequately subject all of the target tissue to meaningful X-ray radiation doses, it may be desirable to visualize the location of the capsule 10 by external means after the capsule 10 has been deployed to the treatment site. Since tungsten is known to act as an X-ray-opaque marker, the capsule 10, which includes inserts 12 having tungsten enriched with tungsten-180, may be visualized, for example, by X-ray examination using an X-ray apparatus external to the body of a patient An important advantage of using tungsten enriched with tungsten-180, in accordance with an embodiment of the invention, is the ability to activate the enriched tungsten to produce the desired radioactive isotope tungsten-181. To produce tungsten-181, the enriched tungsten-180 maybe placed in a high neutron flux, such as that present in a nuclear reactor. In the presence of a high neutron flux, enriched tungsten-180 transmutes to tungsten-181 through neutron capture. Generally, as the only practical source of high neutron flux may be a radiation beam from a nuclear reactor, which beam can emit a mixture of radiation types, it may be desirable to use appropriate filters to enhance the neutron flux spectrum.

Transmutation of enriched tungsten-180 to tungsten-181 occurs relatively slowly within a nuclear reactor neutron flux, and only a small portion of the tungsten-180 may be converted to tungsten-181 at any one time. In particular, after placing the enriched tungsten-180 in the reactor, the amount of tungsten-181 begins to build up, relatively rapidly at first, but then slows down until the rate of tungsten-181 decay is substantially equal to the rate of transmutation of tungsten-180 to tungsten-181. Equilibrium between tungsten-181 decay and tungsten-180 transmutation is typically reached at a tungsten-181 concentration of about 20 atomic percent. In a neutron flux of, for example, 1 E15 n/cm^2/s, the tungsten-181 concentration may reach a level of about 70% of its equilibrium value after 70 days. At about this point, the rate of increase of tungsten-181 percentage may be relatively slow that further exposure to radiation may generally not be of substantial value.

In accordance with an embodiment of the invention, in order to employ the capsule 10 for the treatment protocol of the present invention, activation of tungsten-180 for transmutation to tungsten-181 may be performed either after the insert 12 has been fully assembled within the capsule 10, referred to hereinafter as a "cold process", or just before the insert 12 is assembled in the capsule 10, referred to hereinafter as a "hot process".

In the manufacturing of the capsule 10, if the cold process is employed to activate the tungsten-180, little or no precaution need be taken against radiation exposure during assembly of the capsule 10, since it is only after final assembly that the insert 12 is made radioactive. Moreover, as activation of tungsten-180 is after assembly of the capsule 10, the capsule 10 and insert 12 can be directed to the treatment site shortly thereafter, before any substantial amount of the tungsten-181 decays. It should be appreciated that in the cold process, the capsule 10 is irradiated along with the insert 12. To that end, in the presence of a neutron flux in the reactor, trace impurities within the materials from which the capsule 10 is made may also be activated. Consequently, the materials from which the capsule 10 is made must be chosen from materials that do not contain unacceptable amounts of isotopes that, when irradiated by the neutron flux, would be transmuted to radioactive isotopes that emit undesirable radiations for the treatment of blood vessels. In the event that transmutation does occur, the materials should include those isotopes which have such short half-lives or very low dose rates that their activities have little or no consequence on healthy tissue. Such materials can include, for instance, highly purified aluminum, copper, vanadium, nickel and iron. In cases wherein the material used for capsule 10 may not be biocompatible, an additional outer shell (not shown) made from a biocompatible material may be employed around the capsule 10 after irradiation.

In the hot process, where activation of tungsten-180 is performed on the insert 12 prior to the assembly of the capsule 10, such assembly, in accordance with an embodiment of the invention, may nevertheless be performed relatively quickly, thereby allowing the insert 12 to be delivered thereafter to the treatment site when the activity level of the long half-life tungsten-181 is still at or near maximum. Furthermore, although the hot process requires equipments for shielding technicians who assemble the capsule 10 with a radioactive insert 12, it should be appreciated that there is substantially no concern about transmutation of isotopes present in the materials from which the capsule 10 is made, as such materials are not exposed to any neutron flux. Thus, in the hot process the capsule 10 and/or any other components (e.g., coating) may be made with little concern as to the transmutability of isotopes in those components.

In accordance with an embodiment of the present invention, it may be useful to coordinate the activation and assembly of insert 12 within capsule 10, with patient treatment scheduling. Although an activated insert 12 can be used at any time, the residual tungsten-181 activity decays over time. Accordingly, it may be impractical to use an activated insert 12 in which the tungsten-181 activity has decayed to a level that is relatively low in comparison to its initial activity. Specifically, a low activity level can unreasonably extend the treatment period and extend the period over which a patient is exposed to the radiation.

It should be noted that activation of the insert 12 may not significantly diminish the amount of tungsten-180 distributed therein. Consequently, reactivation of insert 12 in a high neutron flux can provide essentially the same level of activity as that exhibited in a newly manufactured insert 12. In addition, as the cost of tungsten-180-enriched tungsten can be relatively high, the insert 12 can be expensive to produce. As such, to the extent possible, it may be useful to reactivate the insert 12 that has decayed to a low level of activity.

Reactivation of insert 12 can be done on capsule 10 manufactured either by the "cold process" or the "hot process". For a capsule manufactured by the "cold process", the entire capsule 10, including the insert 12 therein, can be exposed to a high neutron flux to reactivate the transmutation of enriched tungsten-180 to tungsten-181. In contrast, for a capsule manufactured by the "hot process" where material for encapsulation may have been selected with little regard for isotope content, the insert 12 may be removed from the capsule 10, reactivated and place in a new capsule 10 or previous capsule 10. The ability to reactivate tungsten-180-enriched tungsten represents an advantage of tungsten relative to other radionuclides used for the purpose of brachytherapy or treating stenosis within a blood vessel.

The capsule 10, made in accordance with embodiments of the present invention, has several advantages. In particular, because of its small size, the capsule 10 can be delivered to the treatment site, for example, through a coronary catheter, with a minimum of tissue trauma. Thereafter, the capsule 10, with the activated insert 12, may be maintained in position at the site of the stenosis or tumorous tissue for a period of time to reduce the occurrence of restenosis or tumor. The capsule 10, may subsequently be removed, also with a minimum of tissue trauma. In addition to the small size of the capsule 10, the generated tungsten-181 isotope has soft therapeutic low energy X-ray radiation and a relatively long 121-day half-life. The low energy radiation can provide a substantially uniform dose distribution to the surrounding tissue, for instance, even with calcification therein and in the presence of a stent. Moreover, the low energy X-ray radiation can simplify radiation protection requirements, and may eliminate the need for expensive isolated heavily shielded facilities.

In accordance with an embodiment of the invention, the low energy X-ray radiation can be adequately shielded by a thin amount of lead (~2 mm). For example, commercially available thin metal shields and lead glass screens can provide protection for the technicians preparing the activated capsule 10 for delivery. Accordingly, when reasonable precautions are taken, i.e., handling the activated capsule 10 by forceps and/or by remote handling devices, and using thin lead shields, medical personnel can expect to face very little exposure to the radiation.

The relatively long half-life of the tungsten-181, on the other hand, provides certain economic benefits. In particular, the insert 12 may be used over a long period of time to treat many patients.

Moreover, if there is to occur a situation whereby the integrity of the capsule 10 or the integrity of the delivery catheter were compromised, the biologically compatible and inert materials from which the capsule 10 is made represent little or no toxicity danger to the patient. Specifically, by encapsulating the insert 12 in a non-toxic capsule 10, any toxic effects of the insert 12 can be minimized. Furthermore, even in the rare event of breach of the capsule 10 or the delivery catheter, and body fluids may gradually seep into the capsule 10, because of the manner in which the insert 12 is made (pressurized to about 75% to 95% of theoretical density), there would be a slow rate of dissolve of materials from the insert 12 into the body of a patient.

Figure 2:
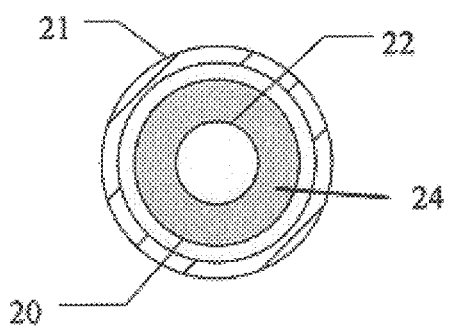
FIG. 2 illustrates a cross-sectional view of the capsule in FIG. 1 in which the X-ray source is distributed within the capsule in accordance with another embodiment of the invention.

Although insert 12 is illustrated in FIG. 1 as a solid insert with tungsten substantially uniformly distributed therethrough, insert 12 may have other configuration. In FIG. 2, an insert 20 is shown positioned within a tube 21 for use in the temporary delivery of X-ray radiation to a treatment site. Insert 20 includes a central core 22 and a layer 24 having substantially uniformly distributed tungsten-180-enriched tungsten in a mixture, compound or alloy metal format. The core 22, as it may be irradiated when the insert 12 is activated in a neutron flux, is preferably made from materials that do not contain unacceptable amounts of isotopes that would be transmuted to radioactive isotopes that emit undesirable radiations for brachytherapy or the treatment of stenosis. Alternatively, if transmutation does occur, the materials from which the core 22 may be made is preferably contain isotopes which when transmuted have short half-lives or very low dose rates that their activities have little or no consequence on healthy tissue. In one embodiment, the materials from which the core may be made includes, highly purified aluminum, copper, vanadium, nickel, iron or oxygen, or alloys or compounds of such materials. The layer 24, circumferentially positioned about the core 22, serves as an X-ray marker for external visualization of the insert 20. In addition, the placement of the tungsten-180-enriched tungsten in layer 24 over the core 22 makes efficient use of the expensive enriched tungsten, while providing an isotropic distribution of emitted X-rays. It should be noted that although the X-ray radiation emitted inward to the core 20 may be substantially absorbed by the core 20, there remains a substantial amount of the low-energy X-ray radiation uniformly emitted by the tungsten-181 radially outwardly to the surrounding tissue from the layer 24. The design of insert 20 provides, in one embodiment, a relative reduction in the quantity of enriched tungsten-180 per unit volume used when compared to the insert 12 in FIG. 1. In addition, the design of insert 20 reduces the amount of self-absorption of the emitted X-ray radiation.

Figure 3:
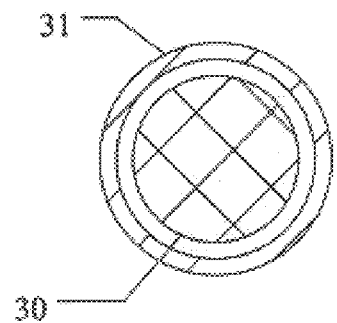
FIG. 3 illustrates a cross-sectional view of the capsule in FIG. 1 in which the X-ray source is distributed within the capsule in accordance with a further embodiment of the invention.

FIG. 3 illustrates a cross-sectional view of an insert 30 in accordance with another embodiment of the present invention. Insert 30, positioned within a tube 31 of a capsule similar to capsule 10, comprises a substantially solid body of low-attenuating (i.e., low-density) material. The tungsten-180-enriched tungsten, used in connection with insert 30, may be provided in either metallic or compound form, and is dispersed as particulates throughout insert 30. The presence of tungsten within the low-attenuating material of insert 30 acts to serve as an X-ray marker for external visualization. Furthermore, the dispersion of the enriched tungsten helps to reduce the self-shielding effect of the tungsten-181-emitted X-ray radiation. In one embodiment of the invention, the low-attenuating material within which the enriched tungsten-180 may be dispersed may be a non-toxic, low-shielding metal or polymer. Examples of low-attenuating polymers include those having elements having atomic numbers in the range of about 1 to about 40, such as silicone polymers or organic polymers (e.g., cross-linked or non-cross-linked). In certain embodiments, the organic polymers can be Teflon, cellulose acetates (including cellulose diacetate), ethylene vinyl alcohol copolymers, hydrogels (e.g., acrylics), polyacrylonitrile, polyvinylacetate, cellulose acetate butyrate, nitrocellulose, polypropylene, polyethylene terephthalate, nylon, polyurethane, polyphenylene oxide blends, polyphenylsulfone, polysulfone, polyether sulfone, polyphenylene sulfide, phenyletheretherketone, polyetherimide liquid crystal polymer, copolymers of urethane/carbonate, copolymers of styrene/maleic acid, and mixtures thereof.

Figure 4:
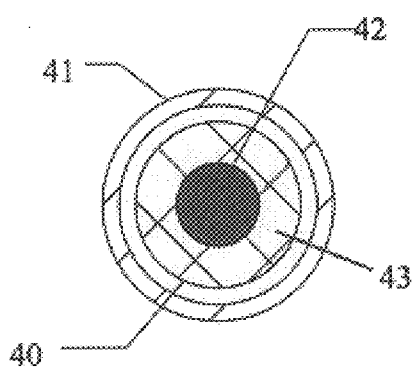
FIG. 4 illustrates a cross-sectional view the capsule in FIG. 1 in which the X-ray source is distributed within the capsule in accordance with still another embodiment of the invention.

FIG. 4 illustrates, in accordance with a further embodiment of the present invention, a cross-sectional view of an insert 40 within a tube 41 of a capsule similar to capsule 10. The insert 40 includes a central core 42 and a layer 43 having substantially uniformly distributed particulates of tungsten-180-enriched tungsten in metallic or compound form. The layer 43, made from a low-attenuating material, is positioned circumferentially about the core 42 and serves as an X-ray marker for external visualization of the insert 40. In one embodiment of the invention, the low-attenuating material may be a non-toxic, low-shielding metal or polymer. The core 42, on the other hand, may be formed from or contain high Z material, including lead, rhodium, gold or tungsten. It should be noted that the dispersion of the enriched tungsten-180 particulates within the layer 43 acts to reduce the self-shielding effect of the tungsten-181-emitted X-ray radiation, while providing uniform radial emission of the X-ray radiation.

While the invention has been described in terms of certain preferred embodiments, modifications obvious to one with ordinary skill in the art may be made without departing from the scope of the invention. For example, whereas the capsule 10 is described herein as preferably containing an insert 12 having an X-ray marker for external visualization, it is to be understood that other methods of visualizing internal organs and materials are coming into increasing use, including CAT scanning and MRI scanning. If visualization of the stenosis or occlusion and the capsule adjacent thereto is contemplated by a method other than by X-ray radiation, it should be appreciated that the capsule is capable of being modified to be detectable by these visualization techniques, for example, by inclusion of a marker particularly adapted for visualization by one of these techniques.

What is claimed is:

1. A device for delivering X-ray radiation to a treatment site, the device comprising:

at least one insert having a non-radioactive X-ray precursor capable of being activated, so as to transform a portion of precursor to an amount of X-ray emitting tungsten-181 with a radiation dose rate sufficient for treatment within a period of one hour; and a capsule within which the insert is placed.

2. A device according to claim 1, wherein X-ray radiation of the dose rate has a range of from about 50 keV to about 70 keV, and wherein the capsule includes a material that is penetrable by X-ray radiation in the range of from about 50 keV to about 70 keV.

3. A device according to claim 1, wherein the non-radioactive X-ray precursor includes tungsten enriched with tungsten-180.

4. A device according to claim 3, wherein the tungsten is enriched to include at least about 30 atomic percent of tungsten-180.

5. A device according to claim 3, wherein the tungsten enriched with tungsten-180 is in powder form.

6. A device according to claim 5, wherein the powder is mixed, compounded or alloyed with other materials.

7. A device according to claim 6, wherein the materials contain minimally acceptable amounts of isotopes that, when irradiated, would be transmuted to radioactive isotopes that emit undesirable radiations for treatment, or if transmuted into radioactive isotopes that emit undesirable radiations, have such short half-lives or low dose rates that their activities have little or no consequence on healthy tissue.

8. A device according to claim 6, wherein the materials include highly purified aluminum, copper, vanadium, nickel, iron and/or oxygen.

9. A device according to claim 1, wherein the insert is in solid form cylindrical in shape.

10. A device according to claim 1, wherein the insert is in wire form.

11. A device according to claim 1, wherein the insert includes a core, and wherein the non-radioactive X-ray precursor is distributed as an outer layer over the core.

12. A device according to claim 11, wherein the precursor includes tungsten enriched with tungsten-180.

13. A device according to claim 12, wherein the tungsten enriched with tungsten-180 is in powder form.

14. A device according to claim 13, wherein the powder is mixed, compounded or alloyed with other materials.

15. A device according to claim 14, wherein the core is made from a material that contain minimally acceptable amounts of isotopes that, when irradiated, would be transmuted to radioactive isotopes that emit undesirable radiations for treatment, or if transmuted into radioactive isotopes that emit undesirable radiations, have such short half-lives or low dose rates that their activities have little or no consequence on healthy tissue.

16. A device according to claim 14, wherein the core includes highly purified aluminum, copper, vanadium, nickel, iron or oxygen, or alloys or compounds thereof.

17. A device according to claim 1, wherein the insert includes a low-attenuating material within which the non-radioactive X-ray precursor is dispersed.

18. A device according to claim 17, wherein low-attenuating material comprises a non-toxic, low-shielding metal or polymer.

19. A device according to claim 17, wherein the precursor includes tungsten enriched with tungsten-180.

20. A device according to claim 19, wherein the tungsten enriched with tungsten-180 is in metallic or compound form.

21. A device according to claim 19, wherein the insert further includes a core and the low-attenuating material within which the tungsten enriched with tungsten-180 is dispersed is provided as a layer positioned over the core.

22. A device according to claim 21, wherein the core is substantially cylindrical in shape and comprises a high Z material, including lead, rhodium, gold or tungsten.

23. A device according to claim 1, wherein the capsule is made from a material that contain minimally acceptable amounts of isotopes that, when irradiated, would be transmuted to radioactive isotopes that emit undesirable radiations for treatment, or if transmuted into radioactive isotopes that emit undesirable radiations, have such short half-lives or low dose rates that their activities have little or no consequence on healthy tissue.

24. A device according to claim 23, wherein the material includes highly purified aluminum, copper, vanadium, nickel, iron or oxygen, or alloys or compounds thereof.

25. A device according to claim 1, wherein the capsule is made from a material that is biocompatible.

26. A device according to claim 25, the biocompatible material includes titanium, stainless steel or nickel-titanium alloy.

27. A method of manufacturing a device for generating X-ray radiation for treatment of diseased tissues, the method comprising:

providing at least one insert having a non-radioactive X-ray precursor capable of being activated, so as to transform a portion of said precursor to an amount of X-ray-emitting tungsten-181; and encasing the insert within a capsule.

28. A method according to claim 27, wherein, in the step of providing, the precursor includes tungsten enriched with tungsten-180.

29. A method according to claim 27, further comprising exposing the capsule with the insert in a neutron flux so as to transform a portion of said precursor to an amount of X-ray-emitting tungsten-181 with a radiation dose rate sufficient for treatment within a period of one hour.

30. A method according to claim 29, further comprising delivering the capsule with the transformed insert to a diseased tissue site.

31. A method of manufacturing a device for generating X-ray radiation for delivery to a treatment site, the method comprising:

providing at least one insert having a non-radioactive X-ray precursor capable of being activated, so as to transform a portion of said precursor to an amount of X-ray-emitting tungsten-181;

exposing the insert in a neutron flux so as to transform a portion of said precursor to an amount of X-ray-emitting tungsten-181 with a radiation dose rate sufficient for treatment within a period of one hour; and encasing the transformed insert within a capsule.

32. A method according to claim 31, wherein, in the step of providing, the precursor includes tungsten enriched with tungsten-180.

33. A method according to claim 31, further comprising delivering the capsule with the transformed insert to a diseased tissue site.

* * * * *